United States Patent [19]

Zhuravlev et al.

[11] 4,408,482

[45] Oct. 11, 1983

[54] METHOD AND APPARATUS FOR THE DETERMINATION OF MOISTURE CONTENT OF FIBROUS AND GRANULAR MATERIALS

[75] Inventors: Vadim F. Zhuravlev, Moscow; Alexei G. Belov, Pushkino, both of U.S.S.R.

[73] Assignee: Tsentralny Nauchno-Issledovatelsky Institut Kozhevenno-Obuvnoi Promyshlennosti, Moscow, U.S.S.R.

[21] Appl. No.: 332,150

[22] Filed: Dec. 18, 1981

[51] Int. Cl.³ .................. G01N 5/00; G01N 25/56; H05B 1/02
[52] U.S. Cl. .................. 73/75; 219/499; 374/43; 374/54; 34/45
[58] Field of Search .............. 73/73, 75; 374/43, 44, 374/54; 219/499; 324/65 R; 34/45, 46, 50

[56] References Cited

U.S. PATENT DOCUMENTS

| 3,195,044 | 7/1965 | Flanagan | 219/499 |
| 3,572,092 | 3/1971 | Zernow | 374/45 |
| 3,803,385 | 4/1974 | Sandorf | 219/499 |
| 3,813,927 | 6/1974 | Furgason | 73/73 |
| 3,818,184 | 6/1974 | Habfast | 219/499 |
| 3,946,199 | 3/1976 | Nakamura | 219/499 |
| 4,251,809 | 2/1981 | Cheney | 73/75 |

FOREIGN PATENT DOCUMENTS

| 272640 | 8/1970 | U.S.S.R. | |
| 389452 | 11/1973 | U.S.S.R. | 73/73 |
| 439730 | 1/1975 | U.S.S.R. | 73/73 |
| 552547 | 3/1977 | U.S.S.R. | |

OTHER PUBLICATIONS

Control and Actuator Devices, Sensors and Relays, Nomenclature Handbook, Moscow, 1979, pp. 19-20.
Automatic Control, Measurement and Recording Instruments, I.V. Butusov, Gosoptekhizdat, Leningrad, 1961, pp. 303-307.

Primary Examiner—Stephen A. Kreitman
Assistant Examiner—David U. Carlson
Attorney, Agent, or Firm—Lilling & Greenspan

[57] ABSTRACT

A method, for the determination of moisture content of fibrous and granular materials, comprising bringing a sensitive element in contact with a fibrous or granular material under study. During the time of contact of the sensitive element with the material under study the sensitive element is subjected to preliminary pulse heating to between 40° and 90° C., with subsequent main pulse heating to between 90° and 140° C. The moisture content of the material under study is evaluated by the time for the main heating of the sensitive element. An apparatus for carrying out the above method comprises main and auxiliary measuring bridge circuits having arms in which are inserted resistors and a sensitive element comprising a pulse heat emitter which forms a common arm of both bridge circuits. A selector switch is inserted in the common arm of the bridge circuits. A zero detector is inserted in the diagonals of the bridge circuits in such a manner that it receives a signal from one bridge circuit in one position of the selector switch and from the other bridge circuit in the other position of the selector switch. To the output of the zero detector is coupled an input of a control unit having its outputs coupled to the selector switch and to a recording instrument.

4 Claims, 3 Drawing Figures

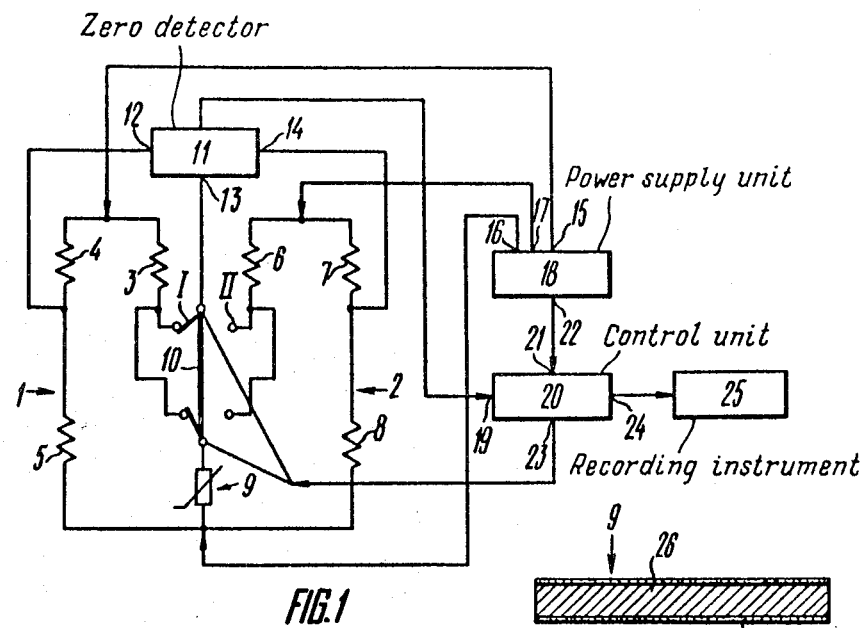
FIG.1
FIG.2
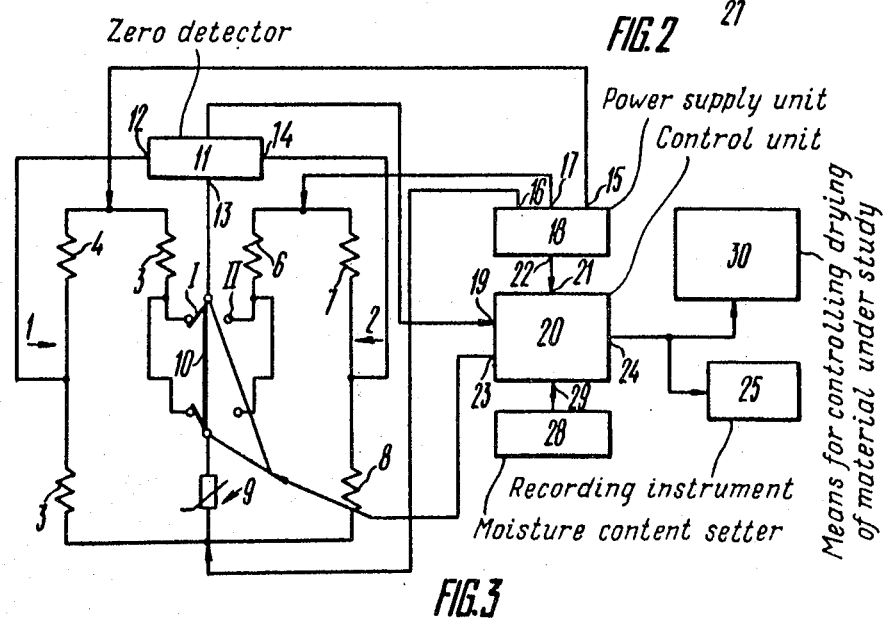
FIG.3

METHOD AND APPARATUS FOR THE DETERMINATION OF MOISTURE CONTENT OF FIBROUS AND GRANULAR MATERIALS

FIELD OF THE INVENTION

The invention relates to measuring devices, and more particularly it deals with a method and apparatus for the determination of moisture content of fibrous and granular materials.

The invention may be used for the determination of moisture content of such materials as leather, fur, fabrics, wood, grain, and it may be employed in the leather and shoemaking industry, in the fur processing and textile industries for controlling the moisture content of the above-mentioned materials during drying.

In determining moisture content of studied materials, e.g. in drying intermediate and finished products, high accuracy and speed of measurements are required. Accurate and rapid measurements of moisture content are also desirable using a comparatively inexpensive apparatus which should have a long service life, the readings of the apparatus being uneffected by temperature and like changes in the physical properties of materials and environment.

DESCRIPTION OF THE PRIOR ART

Known in the art is a method for the determination of moisture content of fibrous materials, comprising studying the kinetics of swelling of polymeric materials. The method consists of placing a sample of a fibrous material under study having a sensitive element in the form of a thermoresistor incorporated therein into a solvent, measuring a change in the current during the removal of the solvent, and determining the degree of swelling by the quantity of energy spent for the removal of the solvent (cf. USSR Inventor's Certificate No. 272640, Cl. G 01 N 13/02).

Known in the art is an apparatus for the determination of moisture content of fibrous materials for carrying out the above-described method, comprising a sensitive element in the form of a thermoresistor which is inserted in a measuring bridge circuit and which is placed together with a sample of a fibrous material under study into a solvent (ibid).

This method is labour-consuming in practice as it requires the employment of a solvent. The presence of additional operations, that is, placing a sample of material into a solvent and swelling of the material, results in a long measurement time. The influence of temperature changes in the environment and material under study makes the measurement rather inaccurate.

The use of a sensitive element in the form of a thermoresistor in the apparatus for carrying out the above-described method does not make it possible to measure moisture content over a wide range of values and limits the field of application of the apparatus.

There is another known method which makes it possible to measure moisture content of fibrous and granular materials more accurately. This method consists of bringing a sensitive element in contact with a fibrous or granular material under study, measuring the dielectrical permeability of the material, and calculating the value of relative humidity using Tables (cf. I.V. Butusov, Automatic Control, Measurement and Recording Instruments (in Russian), Gosoptekhizdat Publ. House, Leningrad, 1961, pp. 303-307).

An apparatus for the determination of moisture content of fibrous and granular materials for carrying out this method comprises a sensitive element in the form of a capacitance sensor which is coupled to a recording device (ibid).

In this method the accuracy of the moisture content measurement is influenced by temperature changes in both the material under study and environment, and obtaining the final result—the value of moisture content—from Tables does not make it possible to measure the moisture content of the material under study in a rapid manner.

In the apparatus for carrying out this method the use of a capacitance sensor for measuring the dielectrical permeability of the material also does not permit rapid measurement of moisture content of the material in real time, so that the field of application of the apparatus is limited.

A method for the determination of moisture content of fibrous and granular materials was contemplated which consists of bringing a sensitive element in contact with a fibrous or granular material under study, and evaluating the moisture content of the material under study in accordance with the information obtained from the sensitive element (cf. USSR Inventor's Certificate No. 552547, Cl. G 01 N 25/56).

An apparatus for the determination of moisture content of fibrous and granular materials for carrying out this methods was also contemplated. The apparatus comprises a main measuring bridge circuit having one arm in which is inserted a sensitive element which is electrically coupled, via a converter, to a recording instrument which makes it possible to evaluate the moisture content of a fibrous or granular material under study (ibid).

The converter of the apparatus for carrying out the method comprises an amplifier having an output to which is connected a circuit consisting of series connected differentiating amplifier, a threshold circuit, a relay of a vacuum pump of a vacuum chamber, this circuit being coupled to a power supply unit via a time delay circuit.

The sensitive element is in the form of a thermoresistor which is placed, together with a sample of a material under study, into a cell installed in a vacuum chamber.

In accordance with the above method, the information from the sensitive element is obtained by measuring a change in the temperature of the material under study, since during vacuum treatment the temperature of the material under study initially starts decreasing as a result of desorption of moisture; concurrently with the temperature decrease, a flow of heat directed from the chamber walls toward the material under study is formed which tends to make their temperatures identical. As the major part of moisture evaporates, the temperature of the material under study starts rising. The temperature of the material under study and its change are sensed by the sensitive element. The temperature information thus obtained from the sensitive element is converted into moisture content thus making the measurement time longer. Placing a sample of the material under study into a vacuum chamber influences the accuracy of the final measurement result.

This method does not make it possible to determine moisture content of materials under natural conditions.

The apparatus for the determination of moisture content for carrying out this method is complicated owing to the use of a vacuum chamber and the above-described converter.

In addition, the error due to the influence of temperature of the material under study and environment is not eliminated so that the range of moisture content measurement is restricted.

SUMMARY OF THE INVENTION

It is an object of the invention to provide a method for the determination of moisture content of fibrous and granular materials which makes it possible to improve the accuracy of moisture content measurement.

Another object of the invention is to provide a method for the determination of moisture content of fibrous and granular materials which also makes it possible to enhance the speed of moisture content measurement.

Still another object of the invention is to provide a method for the determination of moisture content of fibrous and granular materials which makes it possible to measure moisture content of a material under study without sampling and under natural conditions.

It is an object of the invention to provide a simple apparatus reliable in operation for the determination of moisture content of fibrous and granular materials for carrying out the above-mentioned method, which makes it possible to enlarge the range of moisture content measurement.

These objects are accomplished by a method for the determination of moisture content of fibrous and granular materials, consisting of bringing a sensitive element in contact with a fibrous or granular material under study, and evaluating the moisture content of the material under study using the information obtained from the sensitive element. According to the invention, the information from the sensitive element is obtained by applying preliminary pulse heating to the sensitive element to between 40° C. and 90° C. at the moment at which it is brought in contact with the material under study, and main pulse heating to the sensitive element to between 90° C. and 140° C., the moisture content of the material under study being evaluated based on the time for the main heating of the sensitive element.

These objects are accomplished by an apparatus for the determination of moisture content of fibrous and granular materials for carrying out the above method, comprising a main measuring bridge circuit having one arm in which is inserted a sensitive element which is electrically coupled, via a converter, to a recording instrument which is used for evaluating the moisture content of a fibrous or granular material under study. According to the invention, there are provided a plurality of additional resistors coupled to the sensitive element which commprises a pulse heat emitter, the resistors forming together with the heat emitter an auxiliary measuring bridge circuit. A selector switch is inserted in the common arm of the main and auxiliary bridge circuits, and a zero detector is inserted in the diagonals of the main and auxiliary bridge circuits in such a manner that in one position of the selector switch the inputs of the zero detector are connected to the diagonal of the main measuring bridge circuit and a signal from this bridge circuit is fed to the zero detector, and in the other position of the selector switch the inputs of the zero detector are connected to the diagonal of the auxiliary measuring bridge circuit and a signal from this bridge circuit is fed to the zero detector. The converter includes a control unit having its input coupled to the output of the zero detector and outputs coupled to the selector switch and to the recording instrument, respectively.

The apparatus preferably comprises a material moisture content setter having its output coupled to one of the inputs of the control unit.

The apparatus for the determination of moisture content preferably comprises means for controlling drying of the material under study, having an input coupled to one output of the control unit.

The method for the determination of moisture content according to the invention makes it possible to materially improve the accuracy and speed of measurements, obtain moisture content values for materials under natural conditions and in the production processes without sampling and without destruction of the material under study.

The apparatus for carrying out the method according to the invention is simple and it may be manufactured using standard units which are now widely used in the measurement technology; it can control and supervise an optimum drying time. In addition, the apparatus for carrying out the method according to the invention is reliable in operation and has a wide range of moisture content measurement.

BRIEF DESCRIPTION OF THE INVENTION

These and other objects of the invention will become apparent from reading a detailed description of specific embodiments of the invention taken in conjunction with the accompanying drawings, in which:

FIG. 1 is a block-diagram of an apparatus according to the invention for measuring moisture content of fibrous and granular materials for carrying out a method according to the invention;

FIG. 2 is longitudinal sectional view of a sensitive element of the apparatus shown in FIG. 1; and FIG. 3 is a block-diagram of another embodiment of an apparatus for carrying out a method according to the invention.

DETAILED DESCRIPTION OF THE INVENTION

An apparatus for the determination of moisture content of fibrous and granular materials for carrying out a method according to the invention will be described as applied for the determination of moisture content of a studied fibrous material—leather.

A method for the determination of moisture content of a material under study according to the invention comprises bringing a sensitive element in contact with the material under study, and obtaining from the sensitive element information which is used to evaluate the moisture content of the material under study. This information is obtained by applying preliminary pulse heating to the sensitive element to between 40° C. and 90° C. at the moment at which the sensitive element is brought in contact with the material under study and applying main pulse heating to the sensitive element to between 90° C. and 140° C. The moisture content of the material under study is evaluated based on the time of the main heating of the sensitive element.

The temperature of the preliminary heating of the sensitive element is selected at the level of 40° C. because this temperature is an optimum temperature to eliminate the influence of temperatures of the environment and material under study under natural conditions.

The main heating temperature of up to 90° C. is selected at this level because this temperature is adequate for obtaining the moisture content measurement result. In case the sensitive element is heated above 90° C., the sensitivity of the sensitive element is improved, but the time for measuring moisture content becomes respectively longer.

For the determination of moisture content of a material under study by the method according to the invention in drying units, the temperature of preliminary heating of the sensitive element is selected at the level of 90° C. because the temperature of materials, such as leather, in drying units fluctuates between 80° and 85° C. during drying.

A main heating temperature of the sensitive element at the level up to 140° C. is selected since the duration of heating is sufficient for obtaining the moisture content measurement result during drying.

Depending on the kind of material and type of drying process the temperature ranges may be appropriately corrected.

An apparatus for the determination of moisture content of a material under study, according to the invention, which carries out the above-described method, comprises a main measuring bridge circuit 1 (FIG. 1) and an auxiliary measuring bridge circuit 2 having arms in which are inserted resistors 3, 4 and 5 and 6, 7 and 8 and a sensitive element 9, respectively, the sensitive element being a common arm of both bridge circuits. In the common arm of the bridge circuits 1 and 2 is inserted a selector switch 10. A zero detector 11, which is widely known to those skilled in the art, is inserted in the diagonals of the bridge circuits 1 and 2 in such a manner that in one position I of the selector switch 10 inputs 12 and 13 of the zero detector 11 are connected to the diagonal of the bridge circuit 1 and a signal from the main bridge measuring circuit 1 is fed to the zero detector 11, and in the other position II of the selector switch 10 inputs 13 and 14 of the zero detector 11 are connected to the diagonal of the bridge circuit 2 and a signal from the auxiliary measuring bridge circuit 2 is fed to the zero detector 11. The other diagonals of the bridge circuits 1 and 2 are connected to outputs 15 and 16 and 16 and 17, repectively, of a power supply unit 18.

To the output of the zero detector 11 is coupled an input 19 of a converter which comprises a control unit 20 (referred to further as the input 19 of the unit 20). An input 21 of the control unit 20 is coupled to an output 22 of the power supply unit 18. Outputs 23 and 24 of the control unit 20 are coupled to the selector switch 10 and to a recording instrument 25, widely known to those skilled in the art and which is graduated in units of moisture content of the material being studied, respectively.

The control unit 20 may be made as described in the book "Control and Actuator Devices, Sensors and Relays", Nomenclature Handbook, TsNII informatsii i tekhniko-ekonomicheskikh issledovany priborostroenia, sredstv avtomatizatsii, Moscow, 1979, pp. 19–20.

In this embodiment of the apparatus for carrying out the method according to the invention, the sensitive element 9 (FIG. 2) comprises a pulse heat emitter having a plate 26 made of tungsten and placed in an envelope 27 made of a moisture-sensitive material, such as a cloth impregnated with lithium chloride.

The above-described embodiment of the apparatus for carrying out the method according to the invention may be also used in drying units for the determination of moisture content of materials such as leather.

In using the apparatus according to the invention in drying units, there is provided a moisture content setter 28 (FIG. 3) having an output coupled to an input 29 of the control unit 20, and a means 30 for controlling drying of the material under study having its input coupled to the output 24 of the control unit 20. The means 30 comprises a relay.

Basic lines of operation of the apparatus for the determination of moisture content of the material under study for carrying out the method according to the invention reside in the following.

The sensitive element 9 (FIGS. 1, 2) is brought in contact with the material under study (not shown). Power supply is fed through the selector switch 10 (FIG. 1, position I), via the control unit 20, to the main measuring bridge circuit 1, and the balance of the bridge circuit 1 is adjusted, the preliminary heating of the sensitive element 9 being effected to 40° C. for a temperature compensation which is required to eliminate the influence of temperature changes of the material under study and the enviroment on the final result of moisture content measurements. During the preliminary heating of the sensitive element 9 to 40° C. its resistance increases, and the voltage in the diagonal of the main bridge circuit 1 approaches zero value, so that a signal from the zero detector 11 is fed to the control unit 20 which brings the selector switch 10 into position II to energize the auxiliary measuring bridge circuit 2, so that the sensitive element 9 receives the main pulse heating to 90° C.

The heating of the sensitive element 9 to 90° C. causes the voltage in the diagonal of the auxiliary bridge circuit 2 to approach zero value, and a signal from the zero detector 11 is fed to the control unit 20, and the cycle of moisture content measurement is over, the main and auxiliary measuring bridge circuits 1 and 2 are disconnected from the power supply, and the condition of the bridge circuits returns back to the initial state. Then the cycle of operation is repeated.

When the duration of drying of a material to a pre-set moisture content is controlled in drying units, a signal from the moisture content setter 28 (FIG. 3) of the apparatus for carrying out the method, according to the invention, is fed to the control unit 20 where it is compared with a signal carrying information on the moisture content of the material under study. When the pre-set moisture content of the material is achieved, a signal from the control unit 20 is fed to the means 30 for controlling drying of the material under study and to the recording instrument 25, and the drying process is ended.

For supervising the moisture content of the material under study, a preliminary heating temperature in the main bridge measuring circuit 1 is set to a level of 90° C. (somewhat higher than the temperature in drying units), and the auxiliary bridge circuit 2 effects the heating of the sensitive element 9 to 140° C.

For a better understanding of the invention, the following examples illustrating the method for the determination of moisture content of a material under study carried out by the apparatus according to the invention are given below.

EXAMPLE 1

Relative humidity (moisture content) of leather was determined using 300 samples. First, the sensitive element 9 (FIG. 1) was preliminarily heated to 40° C. at the moment of its contact with the leather under study so as to eliminate the influence of the environment and the material under study. Subsequently the main pulse heating of the sensitive element 9 to 90° C. was effected, and the duration of the main heating of the sensitive element 9 was measured by the recording instrument 25 graduated in units of moisture content.

The results of determination of moisture content by the method carried out by the apparatus according to the invention are given below.

| No. | Arithmetical mean of readings (3 series each of 20 samples) | | | Moisture content of sample, % |
|---|---|---|---|---|
| 1 | 2 | 3 | 4 | 5 |
| 1 | 9.00 | 8.99 | 9.01 | 50.7 |
| 2 | 8.69 | 8.63 | 8.70 | 45.7 |
| 3 | 8.01 | 8.02 | 8.04 | 44.1 |
| 4 | 9.64 | 9.60 | 9.70 | 51.7 |
| 5 | 8.60 | 8.62 | 8.59 | 46.2 |
| 6 | 1.95 | 2.07 | 2.07 | 14.9 |
| 7 | 2.40 | 2.46 | 2.25 | 15.6 |
| 8 | 2.16 | 2.25 | 2.22 | 15.7 |
| 9 | 1.95 | 2.10 | 2.01 | 15.0 |
| 10 | 2.01 | 2.07 | 2.10 | 14.3 |

| Number of series | Arithmetical mean | Variance | Rms deviation | Coefficient of variation |
|---|---|---|---|---|
| 6 | 7 | 8 | 9 | 10 |
| 3 | 9.00 | $3.96 \cdot 10^{-4}$ | 0.0196 | 0.0178 |
| 3 | 8.67 | $2.9 \cdot 10^{-5}$ | 0.0054 | 0.011 |
| 3 | 8.02 | $1.6 \cdot 10^{-3}$ | 0.0400 | 0.005 |
| 3 | 9.64 | $1.7 \cdot 10^{-4}$ | 0.0130 | 0.0013 |
| 3 | 8.60 | $1.6 \cdot 10^{-3}$ | 0.0400 | 0.0046 |
| 3 | 2.03 | $3.2 \cdot 10^{-3}$ | 0.0565 | 0.0276 |
| 3 | 2.37 | $1.0 \cdot 10^{-4}$ | 0.0100 | 0.0435 |
| 3 | 2.21 | $1.7 \cdot 10^{-3}$ | 0.0412 | 0.0185 |
| 3 | 2.35 | $1.15 \cdot 10^{-3}$ | 0.0339 | 0.0145 |
| 3 | 2.06 | $1.7 \cdot 10^{-3}$ | 0.0412 | 0.0200 |

EXAMPLE 2

Relative humidity (moisture content) of leather after chrome-zirconium-syntan tanning for footwear bottom during drying was determined.

The sensitive element 9 (FIG. 1) was heated first to 60° C. at the moment of contact with the leather under study, and then the main pulse heating of the sensitive element to 110° C. was effected. The time of the main heating of the sensitive element 9 was measured by the recording instrument 25 graduated in the moisture content units.

EXAMPLE 3

Relative humidity of leather upon achievement of a preset moisture content during vacuum drying in drying units was determined.

The sensitive element 9 (FIG. 3) was preliminarily heated to 90° C., and then the main pulse heating thereof to 140° C. was effected. Upon reaching the pre-set moisture content of the leather the drying unit was turned off.

The apparatus for the determination of moisture content for carrying out the method according to the invention ensures high accuracy and speed of measurements, it has a large range of moisture content measurements, does not damage the materials under study in the measurement zones and determines only the quality of moisture in materials. Impurities in materials and temperature conditions of the environment and materials under study have no effect on readings of the apparatus. The apparatus is capable of instantly reacting to a change in moisture content of the material under study. In addition, the apparatus may control drying of fibrous materials both in one and several drying units. Information on moisture content can be put into a computer in the form of a digital code.

A specific narrow terminology was used in the description of the embodiment of the invention for the sake of clarity. The invention is not, however, limited to the adopted terminology, and it should be kept in mind that each such term covers all equivalents having the same function and intended for similar purposes.

While the invention was described as applied to the preferred embodiment thereof, it is understood that various modifications and embodiments may be used without deviating from the spirit and scope of the invention as it will be apparent to those skilled in the art.

Such modifications and embodiments do not go beyond the spirit and scope of the invention as set forth in the appended claims.

We claim:

1. A method for the determination of moisture content of fibrous and granular materials, comprising the following steps:
   bringing a sensitive element in contact with a fibrous or granular material under study;
   preliminarily applying a pulse heating to said sensitive element at the moment when it is brought in contact with said studied material, to between 40° and 90° C.;
   obtaining information from said sensitive element on said preliminary pulse heating;
   applying a main pulse heating to said sensitive element, to between 90° and 140° C.;
   obtaining an information from said sensitive element on said main pulse heating from said sensitive element; and
   evaluating the moisture content of the studied material upon receiving said information, namely based on the time for the main heating of said sensitive element.

2. An apparatus for the determination of moisture content of fibrous and granular materials, comprising:
   a first measuring bridge circuit having a first arm, a second arm, a third arm, a fourth arm, a first diagonal and a second diagonal;
   first resistors inserted in said first arm, second arm, and third arm, respectively, of the first measuring bridge circuit;
   a sensitive element comprising a pulse heat emitter inserted in the fourth arm of the first measuring bridge circuit;
   a selector switch inserted in the fourth arm of the first measuring bridge circuit;
   a second measuring bridge circuit having a first arm, a second arm, a third arm, a fourth arm which is a common arm with the fourth arm of the first measuring bridge circuit, a first diagonal, and a second diagonal;
   second resistors inserted in the first arm, second arm, and third arm, respectively, of the second measuring bridge circuit;
   a zero detector having a first input, a second input, a third input, and an output, said zero detector being inserted in the first diagonals of the first measuring bridge circuit and second measuring bridge circuit, respectively, so that in one position of said selector switch the first input and the second input of said zero detector are connected to the first diagonal of the first measuring bridge circuit, and said zero detector receives a signal from this bridge circuit, and in the other position of said selector switch the second input and the third input of said zero detector are connected to the first diagonal of the second measuring bridge circuit and said zero detector receives a signal from this measuring bridge circuit;

a control unit having a first input, a second input, a first output, and a second output, the first input being coupled to said output of said zero detector and the second output being coupled to said selector switch;

a recording instrument graduated in units of moisture content of a fibrous or granular material under study, having an input coupled to the second output of said control unit, the moisture content of the material under study being evaluated by means of the recording instrument; and a power supply unit coupled to the second diagonals of the first measuring bridge circuit and second measuring bridge circuit and to the second input of said control unit, respectively.

3. An apparatus according to claim 2, comprising:
said control unit having a third input;
a moisture content setter having an output which is coupled to the third input of said control unit.

4. An apparatus according to claim 3, comprising:
a means for controlling drying of said material under study, having an input which is coupled to said first output of said control unit.

* * * * *